United States Patent [19]

Maggi et al.

[11] 4,272,454
[45] Jun. 9, 1981

[54] PROCESS FOR THE CHLORINATION OF α-AMINOACIDS

[75] Inventors: Rodolfo Maggi; Gian P. Maggi, both of Milan; Guiliano Marcon, Bulciago, all of Italy

[73] Assignee: Chimica Bulciago S.r.l., Bulciago, Italy

[21] Appl. No.: 29,126

[22] Filed: Apr. 11, 1979

[30] Foreign Application Priority Data

May 16, 1978 [IT] Italy .............................. 23446 A/78

[51] Int. Cl.$^3$ .............................................. C07C 51/60
[52] U.S. Cl. .................................................. 260/544 N
[58] Field of Search ....................... 260/544 N, 544 D

[56] References Cited

U.S. PATENT DOCUMENTS 3,869,485  3/1975  DeLong ........................... 260/544 D
3,925,418  12/1975  Williams et al. ................. 260/544 D

OTHER PUBLICATIONS

Hepburn, Derek R. et al., *Chemistry and Industry* (Aug. 1974) pp. 664–665.

Viehe, H. G. et al., *Angew. Chem. internat. Ed.*, vol. 12 (1973), pp. 806–818.
Fieser & Fieser, *Reagents for Organic Synthesis*, vol. I (1967), pp. 286–287.
Zaoral, M. et al., *Tetrahedron Letters*, No. 14 (1960), pp. 9–12.

*Primary Examiner*—Natalie Trousof
*Assistant Examiner*—L. Hendriksen
*Attorney, Agent, or Firm*—Browdy & Neimark

[57] ABSTRACT

A process for the chlorination of the carboxylic group of α-aminoacids is described whereby an aminoacid (e.g. p-hydroxy-phenyl-glycine) is suspended in an anhydrous solvent such as dioxane and treated with a chlorinating agent of the formula:

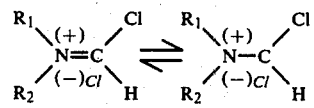

in the presence of HCl in excess. The preferred chlorinating agent is chloromethylene-dimethylammonium chloride.

3 Claims, No Drawings

PROCESS FOR THE CHLORINATION OF α-AMINOACIDS

FIELD OF THE INVENTION

The present invention relates to a process for the chlorination of the carboxylic group of α-aminoacids and, in particular, of p-hydroxy-phenyl-glycine.

DESCRIPTION OF THE PRIOR ART

The chloride of p-hydroxy-phenyl-glycine is an intermediate used in the synthesis of semisynthetic, widely used antibiotics such as amoxycillin.

The chlorination of the carboxylic group of α-aminoacids with usual chlorinating agents such as $PCl_5$, $PCl_3$, $SOCl_2$, etc., often raises difficulties due both to steric hindrances and to the presence of various substituents. Among the aminoacids which are difficult to chlorinate is the p-hydroxy-phenyl-glycine since, for example, the presence of the hydroxyl group on the benzene substituent notably disturbs the formation of the acid chloride.

Among the various attempts made to carry out the chlorination on the carboxylic group of p-OH-phenyl-glycine, a certain degree of success has been obtained by a process based on the use of phosgene as the chlorinating agent. Such a process, which is described in U.S. Pat. No. 3,925,418 as well as by Brenner and Photaki, in Helv. Chimica Acta, 1956, pages 1525–1526, is quite complex since it is based on making a cyclic anhydride and subsequent ring opening thereof with gaseous hydrogen chloride. While the yields obtained are acceptable, the use of phosgene gives rise to notable manufacturing problems due to the known dangers connected with said reactant.

SUMMARY OF THE INVENTION

The applicants, in the course of their studies aimed at obtaining the chlorides of α-aminoacids, have directed their attention toward milder chlorinating agents which would not originate reaction by-products having dangerous chemical characteristics. The most suitable chlorinating agents have been found to be those of the type:

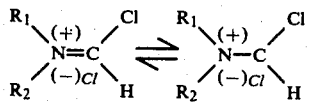

and particularly chloromethylene-dimethylammonium chloride ($R_1=R_2=CH_3$).

This substance, also referred to as dimethyl-chlorophormiminium chloride and already known in literature and used in the chlorination of alcoholic hydroxyl groups (see, for example, D. Hepburn and H. Hudson, Chemistry and Industry, 1974, pages 664–665), has unexpectedly proven to be a chlorinating agent for p-hydroxy-phenyl-glycine under mild conditions.

Chloromethylene-dimethylammonium chloride is prepared by reacting under strictly anhydrous conditions one of the standard chlorinating agents, such as $PCl_5$, $SOCl_2$, $COCl_2$, etc. with an excess of dimethyl-formamide; the resulting crystalline precipitate is washed with an anhydrous solvent, such as dioxane, and is obtained as a white, extremely hygroscopic solid. The preparation of this reactant is described, for example, in Angew. Chem. (Intern.) 12, 1973, page 323 and in Bosshard et. al, Helv. Chimica Acta, 42, 1959, pages 1653–1658.

The chlorination of p-hydroxy-phenyl-glycine is carried out by suspending the latter in dioxane at ambient temperature, saturating the mixture with anhydrous hydrogen chloride to form the hydrochloride of p-hydroxy-phenyl-glycine as a solvate, treating under controlled temperature conditions the mixture thus obtained with chloromethylenedimethylammonium chloride and filtering the crystalline precipitate obtained upon seeding.

As already mentioned, the above described process is also suitable for preparing the acyl chlorides of other aminoacids such as, for example, D(−)α-phenyl-glycine.

The function of the dioxane used as a dispersing agent for p-hydroxy-phenyl-glycine is not only to build up the desired suspension, but also to stabilize the product by forming a solvate in the ratio of one mol of dioxane for two mols of p-hydroxy-phenyl-glycine.

DETAILED DESCRIPTION OF THE PREFERRED EMBODIMENTS

The present invention will now be described in more detail on the basis of two embodying examples given by way of illustration only and not of limitation.

EXAMPLE 1

Preparation of chloromethylene-dimethylammonium chloride.

1200 cc (16.5 mols) of dimethylformamide were introduced into a flask equipped with a stirrer, a thermometer and a thermostatic bath and, while maintaining the temperature at 20° C., 400 g (1.92 mols) of $PCl_5$ were added with stirring, during a one hour period. The resulting solution was cautiously heated up to 40° C. until the crystallization began and cooled down to 0° C. for one hour. The formed precipitate was filtered and washed with 500 cc of ether under anhydrous nitrogen.

500 g of a damp product was obtained which was identified as chloromethylene-dimethylammonium chloride having a titer of 76.6% (1.8 mols) with respect to the damp mass.

EXAMPLE 2

Preparation of the hydrochloride of p-hydroxy-phenyl-glycine chloride as a solvate in dioxane.

50 g (0.3 mols) of anhydrous D(−)p-hydroxy-phenyl-glycine and 400 cc of anhydrous dioxane having a water content of less than 0.02%, as determined by the Karl Fischer test, were charged in a flask equipped with a stirrer, a thermometer and a cooling thermostatic bath and the resulting suspension was saturated at 15° C. with gaseous HCl. 50 g (0.39 mols) of chloromethylenedimethylammonium chloride (100%) obtained according to Example 1 where then added. The exothermic reaction was allowed to take place up to 20° C., thus obtaining a clear solution which was maintained for 2 hours at 20° C. After the addition of 500 mg of seed crystals, the mixture was allowed to crystallize at ambient temperature for 24 hours.

The formed precipitate was filtered, washed with 200 cc of $CH_2Cl_2$ and dried under vacuum at 30° C. It was obtained 50 g (0.18 mols) of the hydrochloride of p-hydroxy-phenyl-glycine chloride in a solvated form having a titer of 82% (theoretical=83.4%), an I.R. spectrum in accordance with the standard and a specific rotation $[\alpha]_D = -97.5°$.

What is claimed is:

1. A process for the chlorination only of the carboxylic group of p-hydroxy-phenyl-glycine consisting essentially of:
   suspending the glycine in an anhydrous solvent at room temperature;
   saturating the suspension with gaseous hydrogen chloride;
   treating the mixture with a stoichiometric amount of chloromethylene-diammonium-chloride while controlling the temperature so as not to exceed 20° C.; and
   filtering the crystalline precipitate product.

2. A chlorination process according to claim 1, wherein said anhydrous solvent is dioxane.

3. A chlorination process according to claim 2, wherein said crystalline precipitate product is the dioxane hemisolvate of (p-hydroxyphenyl)glycyl chloride hydrochloride.

* * * * *

UNITED STATES PATENT AND TRADEMARK OFFICE
CERTIFICATE OF CORRECTION

PATENT NO. : 4,272,454
DATED : June 9, 1981
INVENTOR(S) : MAGGI et al

It is certified that error appears in the above-identified patent and that said Letters Patent are hereby corrected as shown below:

Column 4, line 2, this line should read --chloromethylene-dimethylammonium-chloride while--

Signed and Sealed this

Twenty-second Day of September 1981

[SEAL]

Attest:

GERALD J. MOSSINGHOFF

Attesting Officer

Commissioner of Patents and Trademarks

United States Patent and Trademark Office
CERTIFICATE OF CORRECTION

PATENT NO. : 4,272,454
DATED : June 9, 1981
INVENTOR(S) : MAGGI et al.

It is certified that error appears in the above-identified patent and that said Letters Patent are hereby corrected as shown below:

On the title page
[75] Inventors, line 2, "Guiliano Marcon" should read
--Giuliano Marcon--

[57] Abstract, line 6 and Column 1, line line 45, the structural formula should read:

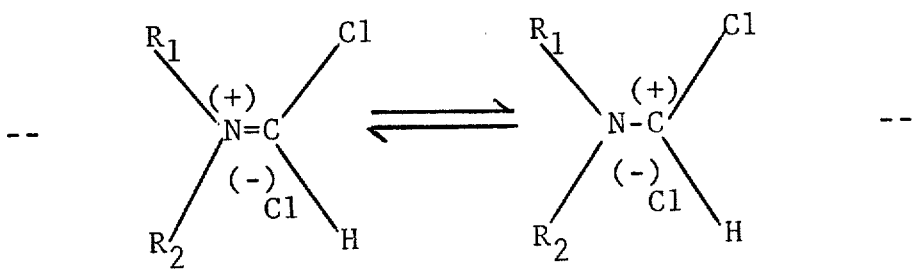

Column 3, line 8, "glycine" should read --p-hydroxy-phenyl-glycine--

Signed and Sealed this

Thirteenth Day of April 1982

[SEAL]

Attest:

GERALD J. MOSSINGHOFF

Attesting Officer     Commissioner of Patents and Trademarks